(12) United States Patent
Ferrera

(10) Patent No.: US 6,432,066 B1
(45) Date of Patent: Aug. 13, 2002

(54) COMPOSITE GUIDEWIRE

(75) Inventor: David A. Ferrera, San Francisco, CA (US)

(73) Assignee: Micrus Corporation, Mountain View, CA (US)

( * ) Notice: Subject to any disclaimer, the term of this patent is extended or adjusted under 35 U.S.C. 154(b) by 7 days.

(21) Appl. No.: 09/710,582

(22) Filed: Nov. 10, 2000

Related U.S. Application Data

(62) Division of application No. 09/221,393, filed on Dec. 28, 1998, now Pat. No. 6,165,140.

(51) Int. Cl.[7] ................................................ A61B 5/00
(52) U.S. Cl. ................................................ 600/585
(58) Field of Search ........................ 600/434, 435, 600/585

(56) References Cited

U.S. PATENT DOCUMENTS

| 679,671 A | 7/1901 | Hannigan |
| 1,341,052 A | 5/1920 | Gale |
| 1,621,159 A | 3/1927 | Evans |

(List continued on next page.)

FOREIGN PATENT DOCUMENTS

| CH | 680041 A5 | 6/1992 |
| DE | 4102550 A1 | 8/1991 |
| EP | 0 183 372 A1 | 6/1986 |
| EP | 0 382014 A1 | 8/1990 |
| EP | 0784991 A2 | 7/1997 |
| FR | 592.182 | 7/1925 |
| GB | 2 066 839 A | 7/1981 |
| WO | WO 98/58697 | 12/1998 |
| WO | WO 99/58183 | 11/1999 |

OTHER PUBLICATIONS

Christos A. Athanasoulis, M.D., The New England Journal of Medicine, May 15, 1980, "Therapeutic Applications of Angiography" pp. 1117–1125 (1 of 2).

Christos A. Athanasoulis, M.D., The New England Journal of Medicine, May 22, 1980, "Therapeutic Applications of Angiography" pp. 1174–1179 (2 of 2).

Alex Berenstein, M.D. and Irwin I. Kricheff, M.D., "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

(List continued on next page.)

Primary Examiner—Max Hindenburg
(74) Attorney, Agent, or Firm—Fulwider Patton Lee & Utecht, LLP; James W. Paul, Esq.

(57) ABSTRACT

The composite guidewire includes an elongated, flexible core formed from a nickel titanium alloy, with a distal tapered portion, a reinforcement tube disposed over the proximal region of the core, a primary coil disposed over the tapered distal region of the core, and a coating of a heat shrinkable material. A distal tip is secured to the distal end of the core. The proximal reinforcement member has a distal tapered portion, to provide for a transition in stiffness of the guidewire. The heat shrinkable coating is formed from an elongated tube of PTFE, and the distal primary coil is formed from one or more nickel titanium alloy strands or wires, one or more platinum wires, or a combination. The distal tip may be formed of platinum or a tantalum filled epoxy.

4 Claims, 1 Drawing Sheet

U.S. PATENT DOCUMENTS

| | | |
|---|---|---|
| 1,667,730 A | 5/1928 | Birchard Green |
| 2,078,182 A | 4/1937 | MacFarland |
| 2,549,335 A | 4/1951 | Rahthus |
| 3,334,629 A | 8/1967 | Cohn |
| 3,417,746 A | 12/1968 | Moore et al. |
| 3,428,611 A | 2/1969 | Brotherton et al. |
| 3,649,224 A | 3/1972 | Anderson et al. |
| 3,670,721 A | 6/1972 | Fukami et al. |
| 3,788,304 A | 1/1974 | Takahashi |
| 3,868,956 A | 3/1975 | Alfidi et al. |
| 4,241,979 A | 12/1980 | Gagen et al. |
| 4,248,910 A | 2/1981 | Pedain et al. |
| 4,257,421 A | 3/1981 | Beal |
| 4,327,734 A | 5/1982 | White, Jr. |
| 4,341,218 A | 7/1982 | Ü |
| 4,402,319 A | 9/1983 | Handa et al. |
| 4,441,495 A | 4/1984 | Hicswa |
| 4,450,246 A | 5/1984 | Jachimowicz |
| 4,473,665 A | 9/1984 | Martini-Vvedensky et al. |
| 4,494,531 A | 1/1985 | Gianturco |
| 4,503,569 A | 3/1985 | Dotter |
| 4,512,338 A | 4/1985 | Balko et al. |
| 4,522,195 A | 6/1985 | Schiff |
| 4,545,367 A | 10/1985 | Tucci |
| 4,585,000 A | 4/1986 | Hershenson |
| 4,638,803 A | 1/1987 | Rand |
| RE32,348 E | 2/1987 | Pevsner |
| 4,655,771 A | 4/1987 | Wallsten |
| 4,690,175 A | 9/1987 | Ouchi et al. |
| 4,692,139 A | 9/1987 | Stiles |
| 4,718,907 A | 1/1988 | Karwoski et al. |
| 4,748,986 A | 6/1988 | Morrison et al. |
| 4,753,222 A | 6/1988 | Morishita |
| 4,753,223 A | 6/1988 | Bremer |
| 4,768,507 A | 9/1988 | Fischell et al. |
| 4,791,913 A | 12/1988 | Maloney |
| 4,795,458 A | 1/1989 | Regan |
| 4,800,882 A | 1/1989 | Gianturco |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,873,978 A | 10/1989 | Ginsburg |
| 4,884,579 A | 12/1989 | Engelson |
| 4,904,048 A | 2/1990 | Sogawa et al. |
| 4,913,701 A | 4/1990 | Tower |
| 4,944,746 A | 7/1990 | Iwata et al. |
| 4,950,258 A | 8/1990 | Kawal et al. |
| 4,954,126 A | 9/1990 | Wallsten |
| 4,957,479 A | 9/1990 | Roemer |
| 4,957,501 A | 9/1990 | Lahille et al. |
| 4,969,709 A | 11/1990 | Sogawa et al. |
| 4,969,890 A | 11/1990 | Sugita et al. |
| 4,976,690 A | 12/1990 | Solar et al. |
| 4,984,581 A | 1/1991 | Stice |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,034,001 A | 7/1991 | Garrison et al. |
| 5,037,404 A | 8/1991 | Gold et al. |
| 5,037,427 A | 8/1991 | Harada et al. |
| 5,041,084 A | 8/1991 | DeVries et al. |
| 5,055,101 A | 10/1991 | McCoy |
| 5,064,435 A | 11/1991 | Porter |
| 5,069,217 A | 12/1991 | Hachecker |
| 5,071,407 A | 12/1991 | Termin et al. |
| 5,089,005 A | 2/1992 | Harada |
| 5,100,429 A | 3/1992 | Sinofsky et al. |
| 5,104,404 A | 4/1992 | Wolff |
| 5,108,407 A | 4/1992 | Geremia et al. |
| 5,122,136 A | 6/1992 | Guglielmi et al. |
| 5,133,364 A | 7/1992 | Palermo et al. |
| 5,133,731 A | 7/1992 | Butler et al. |
| 5,133,732 A | 7/1992 | Wiktor |
| 5,135,517 A | 8/1992 | McCoy |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,151,152 A | 9/1992 | Kaeufe et al. |
| 5,160,341 A | 11/1992 | Brenneman et al. |
| 5,160,674 A | 11/1992 | Colton et al. |
| 5,170,801 A | 12/1992 | Casper et al. |
| 5,171,233 A | 12/1992 | Amplatz et al. |
| 5,176,149 A | 1/1993 | Grenouillet |
| 5,176,625 A | 1/1993 | Brisson |
| 5,176,661 A | 1/1993 | Evard et al. |
| 5,181,921 A | 1/1993 | Makita et al. |
| 5,183,085 A | 2/1993 | Timmermans |
| 5,186,992 A | 2/1993 | Kite, III |
| 5,192,290 A | 3/1993 | Hilal |
| 5,197,978 A | 3/1993 | Hess |
| 5,203,772 A | 4/1993 | Hammerslag et al. |
| 5,211,658 A | 5/1993 | Clouse |
| 5,217,440 A | 6/1993 | Frassica |
| 5,217,484 A | 6/1993 | Marks |
| 5,222,969 A | 6/1993 | Gillis |
| 5,222,970 A | 6/1993 | Reeves |
| 5,224,953 A | 7/1993 | Morgentaler |
| 5,226,911 A | 7/1993 | Chee et al. |
| 5,228,453 A | 7/1993 | Sepetka |
| 5,230,348 A | 7/1993 | Ishibe et al. |
| 5,234,456 A | 8/1993 | Silvestrini |
| 5,238,004 A | 8/1993 | Sahatjian et al. |
| 5,250,071 A | 10/1993 | Palermo |
| 5,258,042 A | 11/1993 | Mehta |
| 5,261,916 A | 11/1993 | Engelson |
| 5,266,608 A | 11/1993 | Katz et al. |
| 5,304,194 A | 4/1994 | Chee et al. |
| 5,308,324 A | 5/1994 | Hammerslag et al. |
| 5,308,342 A | 5/1994 | Sepetka et al. |
| 5,312,152 A | 5/1994 | Woebkenberg, Jr. et al. |
| 5,312,415 A | 5/1994 | Palermo |
| 5,336,205 A | 8/1994 | Zenzen et al. |
| 5,341,818 A | 8/1994 | Abrams et al. |
| 5,342,387 A | 8/1994 | Summers |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,358,493 A | 10/1994 | Schweich, Jr. et al. |
| 5,360,835 A | 11/1994 | Sato et al. |
| 5,366,442 A | 11/1994 | Wang et al. |
| 5,368,049 A | 11/1994 | Raman et al. |
| 5,372,587 A | 12/1994 | Hammerslag et al. |
| 5,373,856 A | 12/1994 | Grenouillet |
| 5,378,236 A | 1/1995 | Seifert |
| 5,382,259 A | 1/1995 | Phelps et al. |
| 5,402,799 A | 4/1995 | Colon et al. |
| 5,409,015 A | 4/1995 | Palermo |
| 5,409,453 A | 4/1995 | Lundquist et al. |
| 5,411,475 A | 5/1995 | Atala et al. |
| 5,413,597 A | 5/1995 | Krajicek |
| 5,423,773 A | 6/1995 | Jimenez |
| 5,423,829 A | 6/1995 | Pham et al. |
| 5,425,806 A | 6/1995 | Doolan et al. |
| 5,437,632 A | 8/1995 | Engelson |
| 5,441,516 A | 8/1995 | Wang et al. |
| 5,443,478 A | 8/1995 | Purdy |
| 5,443,498 A | 8/1995 | Fontaine |

| | | |
|---|---|---|
| 5,472,017 A | 12/1995 | Kovalcheck |
| 5,480,382 A | 1/1996 | Hammerslag et al. |
| 5,484,424 A | 1/1996 | Cottenceau et al. |
| 5,499,973 A | 3/1996 | Saab |
| 5,500,013 A | 3/1996 | Buscemi et al. |
| 5,507,769 A | 4/1996 | Marin et al. |
| 5,507,995 A | 4/1996 | Schweich, Jr. et al. |
| 5,514,128 A | 5/1996 | Hillsman et al. |
| 5,514,176 A | 5/1996 | Bosley, Jr. |
| 5,520,194 A | 5/1996 | Miyata et al. |
| 5,522,836 A | 6/1996 | Palermo |
| 5,525,334 A | 6/1996 | Ito et al. |
| 5,531,685 A | 7/1996 | Hemmer et al. |
| 5,531,716 A | 7/1996 | Luzio et al. |
| 5,533,985 A | 7/1996 | Wang |
| 5,536,235 A | 7/1996 | Yabe et al. |
| 5,540,680 A | 7/1996 | Guglielmi et al. |
| 5,540,712 A | 7/1996 | Kleshinski et al. |
| 5,540,713 A | 7/1996 | Schnepp-Pesch et al. |
| 5,545,210 A | 8/1996 | Hess et al. |
| 5,549,109 A | 8/1996 | Samson et al. |
| 5,549,624 A | 8/1996 | Mirigian et al. |
| 5,554,181 A | 9/1996 | Das |
| 5,562,641 A | 10/1996 | Flomenblit et al. |
| 5,562,698 A | 10/1996 | Parker |
| 5,569,245 A | 10/1996 | Guglielmi et al. |
| 5,571,848 A | 11/1996 | Mortensen et al. |
| 5,578,074 A | 11/1996 | Mirigian |
| 5,582,619 A | 12/1996 | Ken |
| 5,601,593 A | 2/1997 | Freitag |
| 5,603,991 A | 2/1997 | Kupiecki et al. |
| 5,605,162 A | 2/1997 | Mirzaee et al. |
| 5,607,445 A | 3/1997 | Summers |
| 5,614,204 A | 3/1997 | Cochrum |
| 5,622,665 A | 4/1997 | Wang |
| 5,624,461 A | 4/1997 | Mariant |
| 5,624,685 A | 4/1997 | Takahashi et al. |
| 5,636,642 A | 6/1997 | Palermo |
| 5,637,086 A | 6/1997 | Ferguson et al. |
| 5,637,113 A | 6/1997 | Tartaglia et al. |
| 5,638,827 A | 6/1997 | Palmer et al. |
| 5,639,277 A | 6/1997 | Mariant et al. |
| 5,643,251 A | 7/1997 | Hillsman et al. |
| 5,643,254 A | 7/1997 | Scheldrup et al. |
| 5,645,558 A | 7/1997 | Horton |
| 5,645,564 A | 7/1997 | Northrup et al. |
| 5,649,909 A | 7/1997 | Cornelius |
| 5,649,949 A | 7/1997 | Wallace et al. |
| 5,653,691 A | 8/1997 | Rupp et al. |
| 5,660,692 A | 8/1997 | Nesburn et al. |
| 5,662,621 A | 9/1997 | Lafontaine |
| 5,662,622 A | 9/1997 | Gore et al. |
| 5,662,712 A | 9/1997 | Pathak et al. |
| 5,666,968 A | 9/1997 | Imran et al. |
| 5,667,522 A | 9/1997 | Flomenblit et al. |
| 5,669,924 A | 9/1997 | Shaknovich |
| 5,670,161 A | 9/1997 | Healy et al. |
| 5,676,697 A | 10/1997 | McDonald |
| 5,690,643 A | 11/1997 | Wijay |
| 5,690,666 A | 11/1997 | Berenstein et al. |
| 5,690,671 A | 11/1997 | McGurk et al. |
| 5,693,086 A | 12/1997 | Goicoechea et al. |
| 5,695,111 A | 12/1997 | Nanis et al. |
| 5,695,480 A | 12/1997 | Evans et al. |
| 5,695,517 A | 12/1997 | Marin et al. |
| 5,695,518 A | 12/1997 | Laerum |
| 5,700,253 A | 12/1997 | Parker |
| 5,702,361 A | 12/1997 | Evans et al. |
| 5,702,373 A | 12/1997 | Samson |
| 5,702,414 A | 12/1997 | Richter et al. |
| 5,709,704 A | 1/1998 | Nott et al. |
| 5,711,909 A | 1/1998 | Gore et al. |
| 5,716,365 A | 2/1998 | Goicoechea et al. |
| 5,716,410 A | 2/1998 | Wang et al. |
| 5,718,711 A | 2/1998 | Berenstein et al. |
| 5,722,989 A | 3/1998 | Fitch et al. |
| 5,723,004 A | 3/1998 | Dereume et al. |
| 5,725,546 A | 3/1998 | Samson |
| 5,725,568 A | 3/1998 | Hastings |
| 5,733,294 A | 3/1998 | Forber et al. |
| 5,733,329 A | 3/1998 | Wallace et al. |
| 5,733,400 A | 3/1998 | Gore et al. |
| 5,735,816 A | 4/1998 | Lieber et al. |
| 5,741,323 A | 4/1998 | Pathak et al. |
| 5,741,325 A | 4/1998 | Chaikof et al. |
| 5,743,905 A | 4/1998 | Eder et al. |
| 5,746,765 A | 5/1998 | Kleshinski et al. |
| 5,746,769 A | 5/1998 | Ton et al. |
| 5,749,837 A | 5/1998 | Palermo et al. |
| 5,749,891 A | 5/1998 | Ken et al. |
| 5,749,894 A | 5/1998 | Engelson |
| 5,749,921 A | 5/1998 | Lenker et al. |
| 5,755,773 A | 5/1998 | Evans et al. |
| 5,759,173 A | 6/1998 | Preissman et al. |
| 5,769,796 A | 6/1998 | Palermo et al. |
| 5,769,828 A | 6/1998 | Jonkman |
| 5,772,609 A | 6/1998 | Nguyen et al. |
| 5,782,809 A | 7/1998 | Umeno et al. |
| 5,788,626 A | 8/1998 | Thompson |
| 5,788,653 A | 8/1998 | Lorenzo |
| 5,792,055 A | 8/1998 | McKinnon |
| 5,792,124 A | 8/1998 | Horrigan et al. |
| 5,797,842 A | 8/1998 | Pumares et al. |
| 5,797,920 A | 8/1998 | Kim |
| 5,797,957 A | 8/1998 | Palmer et al. |
| 5,800,455 A | 9/1998 | Palermo et al. |
| 5,800,508 A | 9/1998 | Goicoechea et al. |
| 5,807,354 A | 9/1998 | Kenda |
| 5,807,398 A | 9/1998 | Shaknovich |
| 5,814,062 A | 9/1998 | Septka et al. |
| 5,817,126 A | 10/1998 | Imran |
| 5,817,152 A | 10/1998 | Birdsall et al. |
| 5,830,155 A | 11/1998 | Frechett et al. |
| 5,910,364 A | 6/1999 | Miyata et al. |
| 6,019,736 A | 2/2000 | Avellanet et al. |
| 6,142,975 A | 11/2000 | Jalisi et al. |

OTHER PUBLICATIONS

Stephen L. Kaufman, M.D. et al. Investigative Radiology, May–Jun. 1978, "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975, "Selective Arterial Embolization for Control of Massive Upper Gastrointestinal Bleeding" pp. 119–126.

Glenn H. Roberson, et al., American Journal of Radiology, Oct. 1979, "Therapeutic Embolization of Juvenile Angiofibroma" pp. 657–663.

Sidney Wallace, M.D. et al., Cancer, Oct. 1979, "Arterial Occlusion of Pelvic Bone Tumors"; pp. 322–325 & 661–663.

"Mechanical Devices for Arterial Occlusion" By C. Gianturco, M.D., et al., Jul. 1975, pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", By James H. Anderson, et al., Am. J. Roentgenol, Nov. 1977, pp. 795–798.

"'Mini' Gianturco Stainless Steel Coils for Transcatheter Vascular Occlusion" By James H. Anderson, et al., From The Department of Diagnostic Radiology at The University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

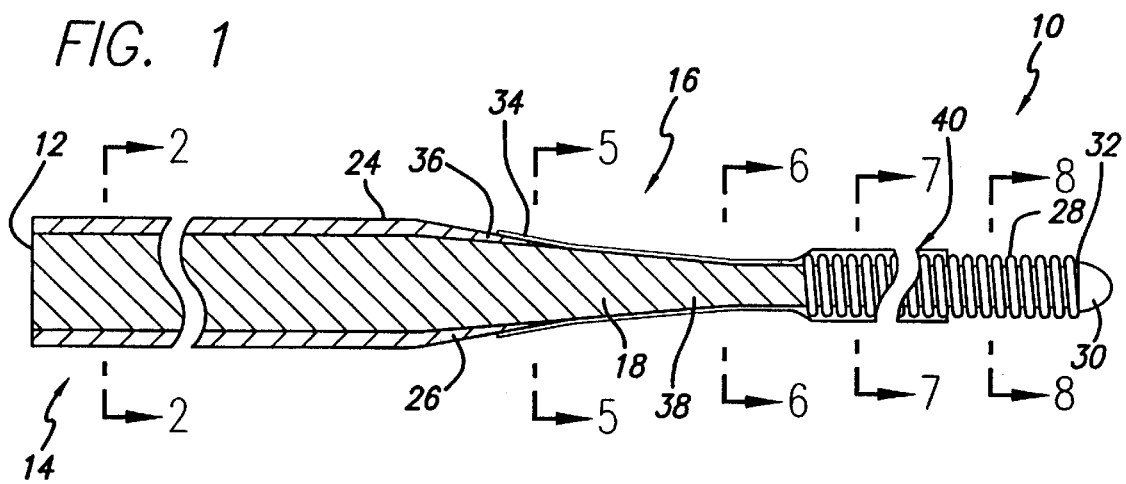
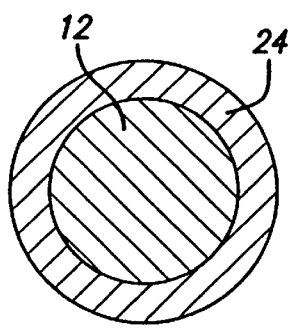
FIG. 2
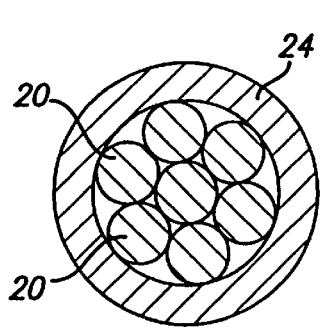
FIG. 3
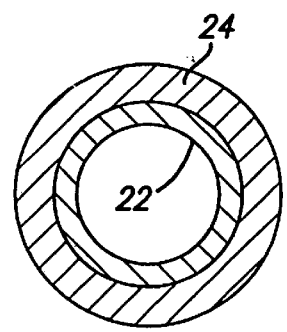
FIG. 4
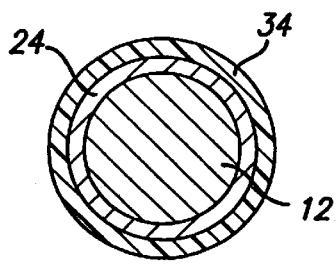
FIG. 5
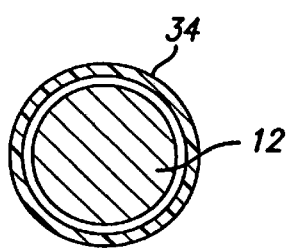
FIG. 6
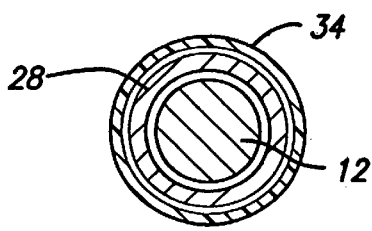
FIG. 7
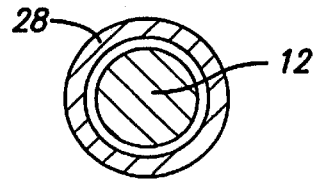
FIG. 8

COMPOSITE GUIDEWIRE

This is a divisional of Ser. No. 09/221,393, filed Dec. 28, 1998 now U.S. Pat. No. 6,165,140.

BACKGROUND OF THE INVENTION

1. Field of the Invention

This invention relates generally to vascular interventional medical devices, and more particularly concerns guide wires for use in a therapeutic system or for delivery of medical devices.

2. Description of Related Art

Conventional minimally invasive catheter based therapies typically require guidewires that are one to two meters long extending through a longitudinal lumen in the catheter, and that are torqueable and pushable at the proximal end, yet soft and flexible at the distal end. Many such guidewires are made of stainless steel or the like, and are ground to tapers which provide the desired bending properties along the guidewire. It is useful for such guidewires to be torqueable from the base of the guidewire for manipulation of the distal tip, which is typically bent, for guiding the distal tip through vascular passages. While such guidewires need to be torqueable, pushable and resilient, particularly at the proximal regions of the guidewire, they also need to be flexible, particularly at the distal regions of the guidewire.

One prior guidewire for use with a catheter includes a core wire formed from a nickel titanium alloy, with a tapered distal tip portion and a distal end cap, covered by a sheath of material such as polyurethane, polyethylene, nylon, silicone, polytetrafluoroethylene, cellulose, starch or gelatin. Another prior guidewire comprises a composite guidewire with a core of stainless steel or a nickel titanium alloy, a tapered distal region ending in a distal flexible coil and end cap, also having a major portion of the guidewire covered by a thin layer of polymeric material, such as polysulfones, polyfluorocarbons, polyolefins, polyesters, polyamides, polyurethanes, blends and copolymers such as polyether block amides.

However, there remains a need for a guidewire with enhanced proximal stiffness, with a stiff, high modulus reinforcement, allowing for greater manipulation of the guidewire by the physician, along with greater distal tip flexibility with radiopacity. The present invention meets these needs.

SUMMARY OF THE INVENTION

Briefly, and in general terms, the present invention provides an improved composite guidewire with a proximal high modulus reinforcement member for promoting greater proximal stiffness, with a tapered distal region and distal radiopaque coil providing greater distal tip flexibility with radiopacity. The composite structure thus advantageously provides for a composite guidewire with greater resilience, a transition in stiffness, and tip flexibility. The proximal stiffer, high modulus member, covering or reinforcing a nickel alloy core, can be formed of high modulus metals such as stainless steel, titanium, and the like, allowing for greater manipulation of the guidewire by the physician, while the distal coil has enhanced durability, being formed from a composite strand of a nickel titanium alloy and platinum.

The present invention accordingly provides for a composite guidewire having an elongated, flexible core formed from a nickel titanium alloy having proximal and distal regions, with the distal region having a tapered portion, a reinforcement tube disposed over the proximal region of the core, a primary coil disposed over the tapered distal region of the core, with a coating of a heat shrinkable material disposed over at least a portion of the reinforcement member, an intermediate portion of the core, and at least a portion of the primary coil, and a distal tip secured to the distal end of the core.

In a presently preferred embodiment, the core is a nickel titanium alloy rod, although the core may alternatively be formed of one or more elongated strands of nickel titanium alloy, or an elongated tube. In another presently preferred aspect, the proximal reinforcement member is formed as an elongated ground stainless steel hypo tube, although the reinforcement member may alternatively be formed of an elongated tube made of titanium, or a nickel titanium alloy. In another presently preferred aspect, the proximal reinforcement member is formed with a distal tapered portion, to provide for a transition in stiffness of the guidewire. In a presently preferred embodiment, the heat shrinkable coating is formed from an elongated tube of polytetrafluoroethylene (PTFE), although the heat shrinkable coating may also be selected from other heat shrinkable materials such as polyethylene, for example. In another presently preferred aspect of the invention, the distal primary coil is formed from one or more nickel titanium alloy strands or wires, and in another presently preferred aspect the distal primary coil is formed from one or more platinum wires, or a combination of one or more nickel titanium alloy strands and one or more platinum wires. In one currently preferred embodiment, the distal tip is formed of platinum, and is bonded to the distal end of the core such as by welding, or soldering, or the like, although the distal tip may also be formed of other materials such as a tantalum filled epoxy adhesively bonded to the distal end of the core.

These and other aspects and advantages of the invention will become apparent from the following detailed description and the accompanying drawings, which illustrate by way of example the features of the invention.

BRIEF DESCRIPTION OF THE DRAWINGS

FIG. 1 is a longitudinal sectional schematic diagram of the composite guidewire of the invention;

FIG. 2 is a transverse sectional view taken along line 2—2 of FIG. 1;

FIG. 3 is a transverse sectional view similar to FIG. 2 illustrating a first alternate preferred embodiment;

FIG. 4 is a transverse sectional view similar to FIG. 2 illustrating a second alternate preferred embodiment;

FIG. 5 is a transverse sectional view taken along line 5—5 of FIG. 1;

FIG. 6 is a transverse sectional view taken along line 6—6 of FIG. 1;

FIG. 7 is a transverse sectional view taken along line 7—7 of FIG. 1;

FIG. 8 is a transverse sectional view taken along line 8—8 of FIG. 1.

DETAILED DESCRIPTION OF THE PREFERRED EMBODIMENTS

Guidewires used for vascular therapeutic intervention typically need to be torqueable, pushable and resilient over a proximal region of the guidewire, and flexible, over the distal region of the guidewire. While tapered guidewires can provide a range of proximal stiffness and torqueability to distal flexibility, enhancement of the proximal stiffness of such guidewires can give a physician manipulating the guidewire better control over the distal positioning of the guidewire.

As is illustrated in the drawings, the invention is embodied in a composite guidewire 10 illustrated in FIG. 1, having a central elongated, flexible core 12 preferably formed from a nickel titanium alloy such as Nitinol, having a proximal region 14 and a distal region 16. The distal region of the core preferably includes a tapered portion 18, to provide for a gradual transition to increased flexibility in the distal region of the guidewire. The core is preferably formed as an elongated rod, as illustrated in FIG. 2, although the core may also be formed of a one or more strands 20 of a nickel titanium alloy such as Nitinol as shown in FIG. 3. The one or more strands may be helically wound, or may run longitudinally parallel along the length of the guidewire. Alternatively, the core may also be formed from an elongated tube 22 such as a hypo tube made of a nickel titanium alloy such as Nitinol, as shown in FIG. 4.

A proximal reinforcement tube 24 is preferably disposed over the proximal region of the core, with the reinforcement tube preferably having a tapered distal portion 26, to provide for a transition in stiffness of the guidewire. The proximal reinforcement member is currently preferably formed from an elongated ground stainless steel hypo tube, although the reinforcement member may alternatively be formed of an elongated tube made of titanium, or a nickel titanium alloy such as Nitinol.

A primary coil 28 is preferably bonded over the tapered distal region of the core, such as by welding, solder, or by adhesive such as cyanoacrylate. The primary coil is currently preferably formed from one or more nickel titanium alloy strands or wires as described above, one or more platinum wires to provide radiopacity to the primary coil, or a combination of one or more nickel titanium alloy strands and one or more platinum wires. A distal tip 30 is preferably secured to the distal end 32 of the core and to the distal end 32 of the primary coil. In one currently preferred embodiment, the distal tip is formed of platinum, and is bonded to the distal end of the core such as by welding, or soldering, or the like, although the distal tip may also be formed of other materials such as a tantalum filled epoxy adhesively bonded to the distal end of the core and to the distal end of the primary coil.

An outer coating of a heat shrinkable polymeric material 34, such as an elongated tube of polytetrafluoroethylene (PTFE), is also preferably disposed over at least a distal portion of the reinforcement member 36, an intermediate portion 38 of the core, and at least a portion 40 of the distal primary coil. The heat shrinkable coating may also be selected from other similar suitable heat shrinkable materials such as polyethylene, for example.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A composite guidewire, comprising:

an elongated, flexible core, said core having proximal and distal regions, with said distal region having a tapered portion;

a reinforcement tube disposed over said proximal region of said core, said reinforcement tube including a distal tapered portion extending over said tapered portion of said elongated, flexible core;

a primary coil disposed over said tapered distal region of said core;

a coating of a heat shrinkable material disposed over said distal tapered portion of said reinforcement tube, said tapered portion of said core, and at least a portion of said primary coil; and a distal tip secured to the distal end of said core.

2. The composite guidewire of claim 1, wherein said elongated, flexible core comprises a rod.

3. The composite guidewire of claim 1, wherein said elongated, flexible core comprises at least one strand.

4. The composite guidewire of claim 1, wherein said elongated, flexible core comprises a hypo tube.

* * * * *